(12) United States Patent
Zaphrir et al.

(10) Patent No.: US 11,568,993 B2
(45) Date of Patent: Jan. 31, 2023

(54) SYSTEM AND METHOD OF PREDICTING A HEALTHCARE EVENT

(71) Applicant: OWLYTICS HEALTHCARE LTD, Bnei-Atarot (IL)

(72) Inventors: Gill Zaphrir, Bnei Atarot (IL); Yaron Recher, Ramat Yishai (IL); Ronen Feldman, Petach Tikva (IL)

(73) Assignee: OWLYTICS HEALTHCARE LTD, Bnei-Atarot (IL)

( * ) Notice: Subject to any disclaimer, the term of this patent is extended or adjusted under 35 U.S.C. 154(b) by 698 days.

(21) Appl. No.: 15/896,098

(22) Filed: Feb. 14, 2018

(65) Prior Publication Data

US 2018/0174686 A1  Jun. 21, 2018

Related U.S. Application Data

(63) Continuation-in-part of application No. PCT/IL2016/050890, filed on May 16, 2016.
(Continued)

(51) Int. Cl.
*G16H 50/30* (2018.01)
*A61B 5/00* (2006.01)
(Continued)

(52) U.S. Cl.
CPC ........... *G16H 50/30* (2018.01); *A61B 5/0022* (2013.01); *A61B 5/7267* (2013.01);
(Continued)

(58) Field of Classification Search
CPC combination set(s) only.
See application file for complete search history.

(56) References Cited

U.S. PATENT DOCUMENTS 8,388,530 B2 *  3/2013  Shusterman
9,257,029 B1 *  2/2016  Hendrick, III et al.
(Continued)

FOREIGN PATENT DOCUMENTS

WO  WO 2014/060938  4/2014

OTHER PUBLICATIONS

Extended Search Report for EP App. No. 16836746.4 dated May 6, 2019.
Office Action for CN App. No. 2016800597217 dated Mar. 1, 2021.

*Primary Examiner* — Michael Tomaszewski
*Assistant Examiner* — William T. Monticello
(74) *Attorney, Agent, or Firm* — Pearl Cohen Zedek Latzer Baratz LLP

(57) ABSTRACT

A method of predicting a healthcare event includes: receiving via an input device, classifying personal information for each of a plurality of persons; collecting measurements of at least one health indicator during a predefined learning period; creating a personal physiological pattern profile, based on the collected data; associating each of the plurality of persons to a physiological cluster based on each person's personal physiological pattern profile and based on the classifying personal information of each of the plurality of persons; creating, for each physiological cluster, a health indicator deviation pattern for the healthcare event; continuously monitoring values of the health indicator of the person; and determining an occurrence probability of the healthcare event when the monitored indicators deviate from the personal physiological pattern profile. A system for predicting a healthcare event is also disclosed.

22 Claims, 9 Drawing Sheets

Related U.S. Application Data

(60) Provisional application No. 62/206,323, filed on Aug. 18, 2015.

(51) Int. Cl.
| | |
|---|---|
| *G16H 10/60* | (2018.01) |
| *G16H 50/70* | (2018.01) |
| *G06F 1/16* | (2006.01) |
| *G06F 3/01* | (2006.01) |
| *A61B 5/0533* | (2021.01) |
| *A61B 5/021* | (2006.01) |
| *A61B 5/024* | (2006.01) |
| *A61B 5/11* | (2006.01) |
| *A61B 5/08* | (2006.01) |
| *A61B 5/01* | (2006.01) |

(52) U.S. Cl.
CPC .............. *A61B 5/7275* (2013.01); *A61B 5/74* (2013.01); *G06F 1/163* (2013.01); *G06F 3/011* (2013.01); *G16H 10/60* (2018.01); *G16H 50/70* (2018.01); *A61B 5/01* (2013.01); *A61B 5/021* (2013.01); *A61B 5/02405* (2013.01); *A61B 5/02438* (2013.01); *A61B 5/0533* (2013.01); *A61B 5/0816* (2013.01); *A61B 5/11* (2013.01); *A61B 5/1112* (2013.01); *A61B 5/4806* (2013.01)

(56) References Cited

U.S. PATENT DOCUMENTS

| | | | |
|---|---|---|---|
| 2006/0241510 | A1* | 10/2006 | Halperin et al. |
| 2007/0191697 | A1* | 8/2007 | Lynn et al. |
| 2011/0004110 | A1 | 1/2011 | Shusterman |
| 2012/0245439 | A1* | 9/2012 | Andre et al. |
| 2015/0118658 | A1* | 4/2015 | Mayou et al. |
| 2015/0347698 | A1* | 12/2015 | Soni et al. |
| 2017/0242975 | A1* | 8/2017 | Kahlbaugh |
| 2019/0069154 | A1* | 2/2019 | Booth et al. |

* cited by examiner

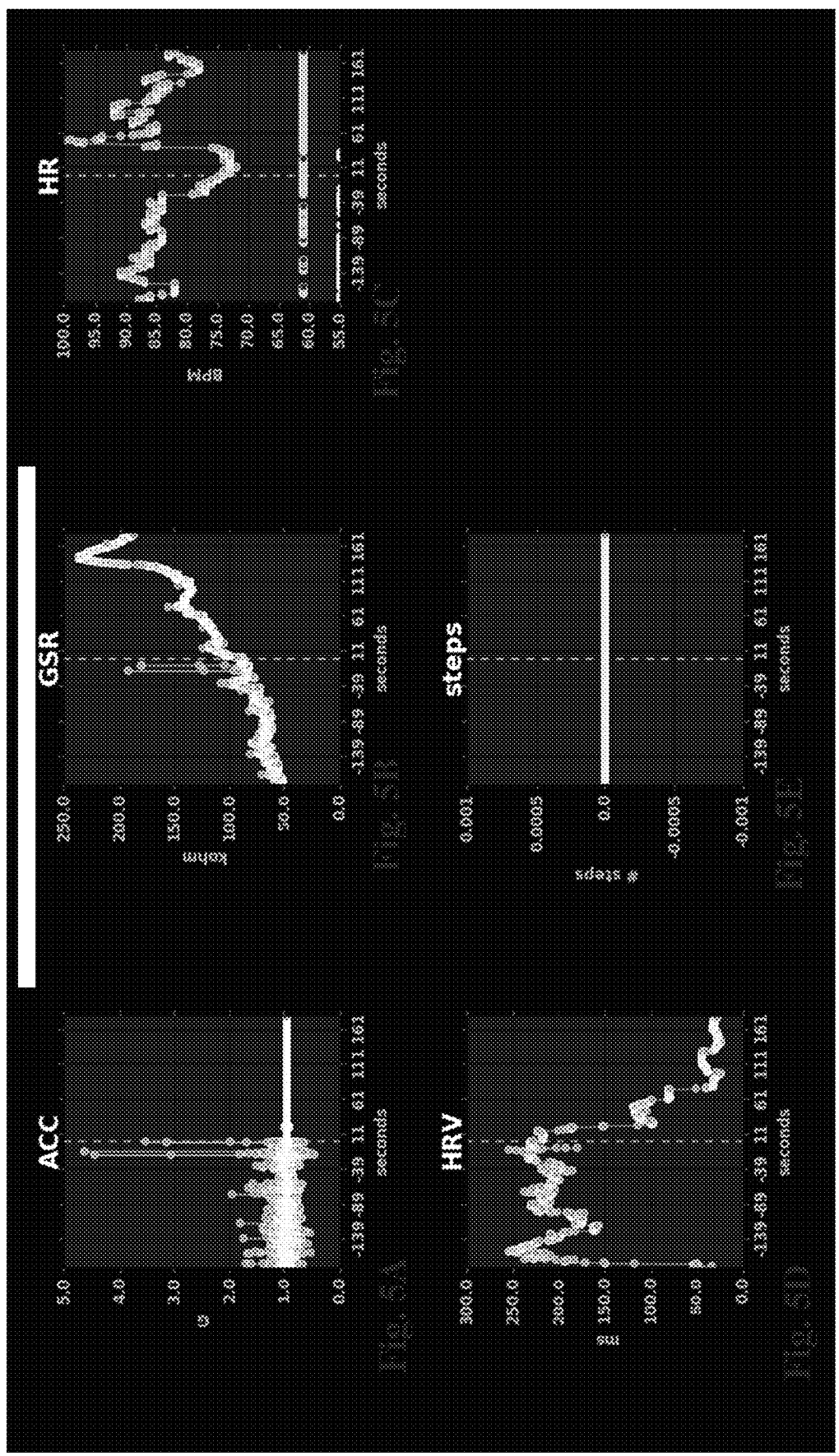

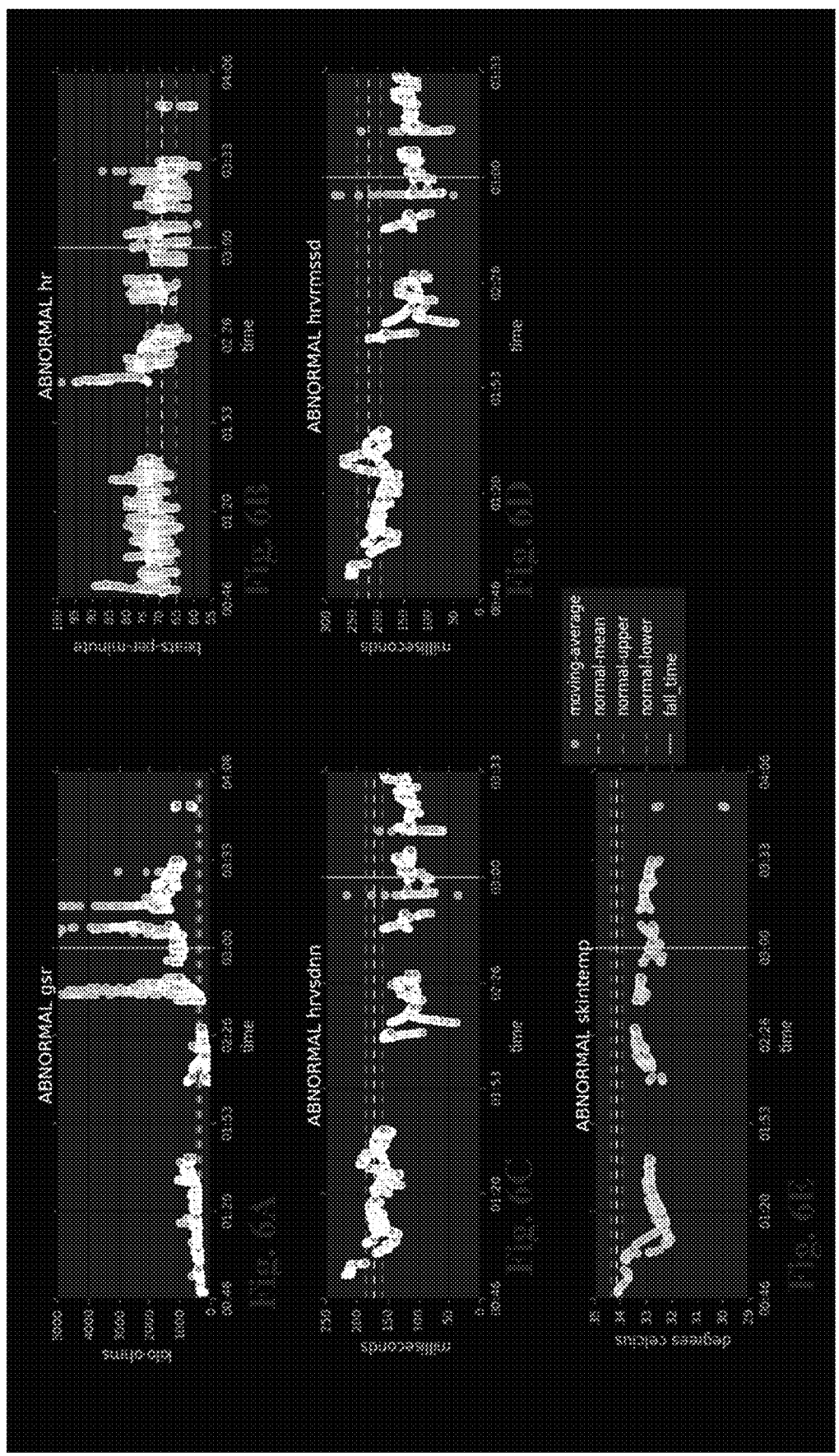

SYSTEM AND METHOD OF PREDICTING A HEALTHCARE EVENT

CROSS REFERENCE TO RELATED APPLICATIONS

This application is a continuation in part of International Patent Application No. PCT/IL2016/050890 filed on Aug. 16, 2016 and entitled "SYSTEM AND METHOD OF PREDICTING A HEALTHCARE EVENT" which claims the benefit of U.S. Provisional Application No. 62/206,323, filed on Aug. 18, 2015, which are incorporated in their entirety herein by reference.

FIELD OF THE INVENTION

The present invention relates generally to prediction of healthcare events. More specifically, the present invention relates to using portable devices for predicting a medical event is expected and providing an alert.

BACKGROUND OF THE INVENTION

Portable computing devices such as wearable devices (e.g. smart watches, smart glasses etc.) and other mobile devices (e.g. smartphones) are in wide use worldwide. Such devices are capable of collecting a wide range of data regarding the user of such devices.

However, while such devices may provide cumulative information regarding the collected data, such as the duration of a training session, the average, minimum and maximum heart rate during a training session, the distance reached during such training session etc. Such devices are incapable of providing any predictions regarding expected events such as medical or healthcare events.

SUMMARY OF THE INVENTION

Embodiments of the present invention provide a system and method for predicting a healthcare event. Such a system and a method may dramatically reduce the time for detection of the healthcare event and improve the accuracy of the determination in comparison to known prior art methods and devices. Embodiments of the invention may utilize computerized methods of continuous monitoring of physiological indicators of a person in order to predict and/or determine, in real time, the occurrence of a healthcare event (e.g., a fall, a heart attack, etc.). Such embodiments may allow a quicker provision of the correct medical treatment. Embodiments of the invention may use data collected from the continuous monitoring, over time, as a base-level or a range for physiological indicators of the person and compare the persons real-time monitored physiological indicators to his own physiological parameters to determine a deviation from a normal behavior. This continuous computerized monitoring and comparing may lead to an accurate prediction and/or determination, in real time, of the occurrence of the healthcare event.

According to one embodiment a method of predicting a healthcare event may include: receiving via an input device associated with a person, classifying personal information for the person; collecting, via at least one sensor associated with the person, measurements of at least one health indicator of the person, during a predefined period and creating, by a controller, a personal physiological pattern profile for the person. According to some embodiments a method may further include: associating the person to or with a physiological cluster based on the created personal physiological pattern and the classifying personalized information; continuously monitoring, via the at least one sensor, the measurements of the at least one health indicator of the person; determining an occurrence probability of the healthcare event when a pattern of the monitored measurements deviate from patterns associated with the physiological cluster to which the person was associated, received from a database, and detecting a healthcare event when the occurrence probability of the health event is higher than a predefined threshold.

According to some embodiments, the healthcare event may be at least one of: cardiac arrest, stroke, viral influenza, pre-eclampsia, oxygen drop, overheating, being over active, fall, pre-dehydration, abnormal physiologic deviation, fatigue and anxiety.

The health indicators, according to some embodiments, may consist of one or more of: heart rate, heart rate variability, respiration rate, acceleration, location, movement, Galvanic Skin Response (GSR), oxygen saturation, $CO_2$ blood level, skin temperature, sleeping hours, blood pressure, and physiological state.

According to some embodiments, the physiological state may be received from a person via an input device. The physiological state may consist of one or more of: sleep, rest, moderate activity, intense activity and sport competition.

According to some embodiments, creating a personal physiological indicators profile may include obtaining a plurality of measurements of each physiological indicator, from a wearable device, in a first physiological state, obtaining a plurality of measurements of each physiological indicator, from the wearable device, in at least a second physiological state; and calculating, by a processor, a range of normal values for each physiological indicator, in each physiological state, based on the obtained measurements and based on the one or more clusters to which the at least one person is associated.

According to some embodiments of a method according to the present invention, the association of a person to a cluster may be based on at least one of: gender, weight, height, age, ethnic association, fitness level, daily and weekly activity level, body mass index (BMI) and the collected values of the one or more health indicators. Other parameters may be used.

According to some embodiments a method, may further include issuing an alert when the occurrence probability of the health event is higher than a predefined threshold value.

According to some embodiments, a method may further include sending a feedback request to a user of the computing device, such as a mobile device, when a deviation from the at least one person's personal physiological pattern profile is identified. According to some embodiments, According to some embodiments a method may further include updating the personal physiological pattern profile of the at least one person based on monitored health indicators and healthcare events history.

According to some embodiments a method, may further include measuring additional health indicators based on previously measured health indicators and based on the feedback received from the at least one person.

According to some embodiments, when the healthcare event occurs, a method may further include updating the physiological cluster's deviation pattern of the healthcare event based on the at least one health indicator's values measured during a predefined time period prior to the occurrence of the healthcare event. An indication that the healthcare event has occurred may be received, according to some embodiments, from a health maintenance provider and/or from at least one person.

A system for predicting a healthcare event, according to embodiments of the present invention may include: a first communication unit configured to receive health indicator values from a portable user device, a database configured to store one or more of: health indicator values; physiological cluster information; healthcare events information; and personal information of a plurality of persons and a main controller. In some embodiments, the portable computing device may include a controller, at least one sensor adapted to measure at least one health indicator value and a second communication unit configured to communicate with the first communication unit and transmit measured health indicator values to the main controller. In some embodiments, the main controller may be configured to: receive via an input device associated with a person, classifying personalized information for the person, collect, from the at least one sensor, measurements of at least one health indicator of the person, during a predefined period, create a personal physiological pattern profile for the person, associate the person to a physiological cluster based on the created personal physiological pattern and the classifying personal information, continuously monitor, via the at least one sensor, values of the at least one health indicator of the person and determine an occurrence probability of the healthcare event when the monitored values deviate from values associated with the physiological cluster to which the person was associated, received from the database.

According to some embodiments the database may be adapted to store one or more of: physiological cluster information; healthcare events information; and personal information of a plurality of persons.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 5A-5E are graphs of measurements of physiological indicators before and after a fall event according to some embodiments of the invention;

FIGS. 6A-6E are graphs of measurements of physiological indicators measured during a predefined period according to some embodiments of the invention.

Figure 1:
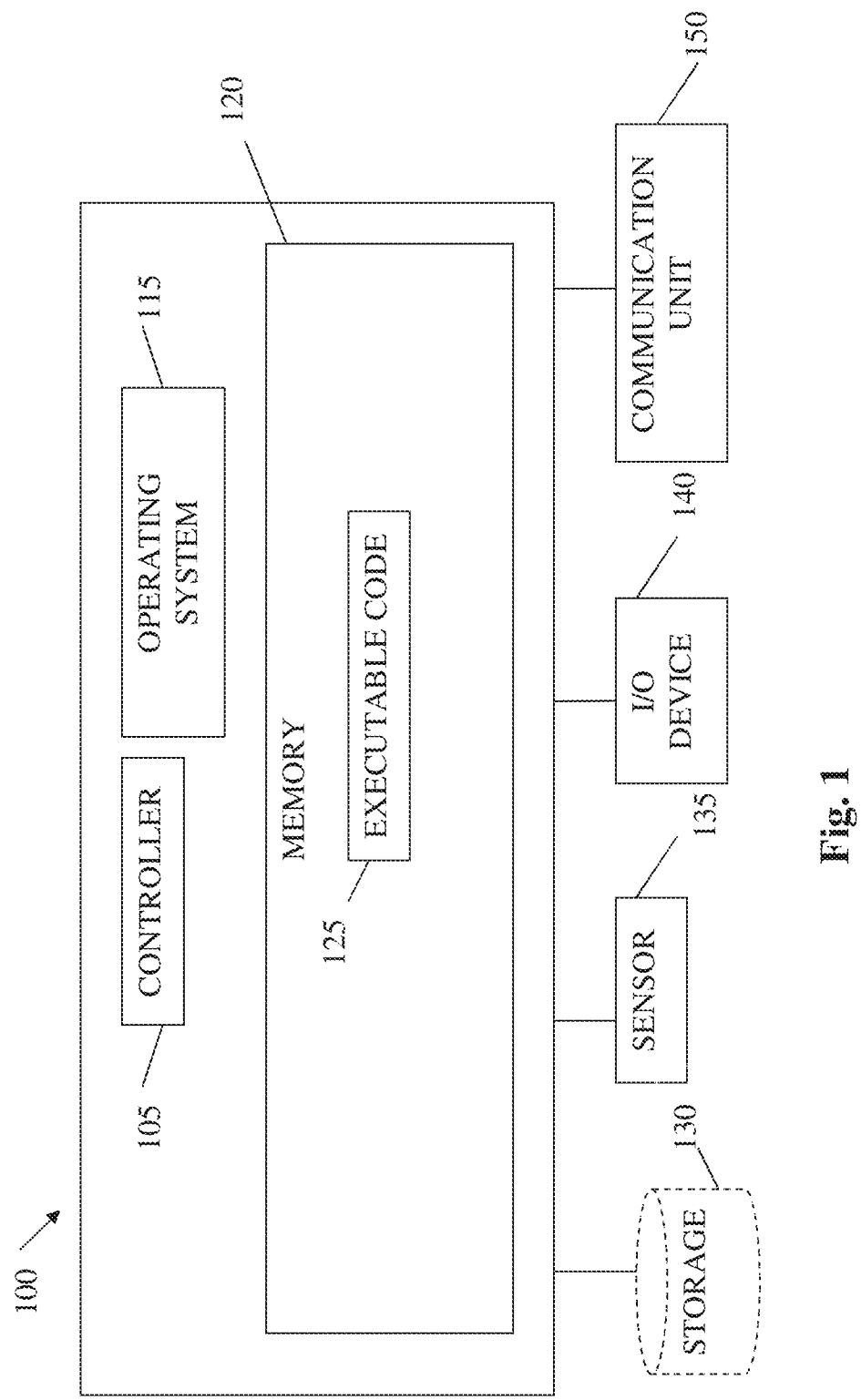
FIG. 1 shows high level block diagram of an exemplary portable device according to embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing", "computing", "calculating", "determining", "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, embodiments described herein are not constrained to a particular order or sequence. Additionally, some of the described method embodiments or elements thereof can occur or be performed simultaneously, at the same point in time, or concurrently.

Reference is made to FIG. 1, showing a high level block diagram of an exemplary portable or mobile device according to embodiments of the present invention. Portable device 100 may include a controller 105 that may be, for example, a central processing unit processor (CPU), a chip or any suitable computing or computational device, an operating system 115, a memory 120, executable code 125, a storage 130, sensor 135 that may include, one or more sensors, such as heart rate sensor, respiration rate sensor, oxygen saturation sensor, $CO_2$ level sensor, motion sensor, accelerometer, Global Positioning System (GPS) sensor, thermometer, Galvanic Skin Response (GSR) sensor, or any other sensor configured to measure vital signs and other health indicators known in the art, and input/output devices 140 that may include, for example, a keyboard, a touch screen, a display or the like. Portable device 100 may further include, a communication unit 150 (e.g. a Bluetooth communication unit, a Wi-Fi communication unit, an infrared (IR) communication unit or the like) for communicating with remote devices via a communication network, such as, for example, the Internet.

Controller 105 may be configured to carry out methods described herein, and/or to execute or act as the various modules, units, etc. More than one portable device 100 may be included, and one or more portable devices 100 may act as the various components, for example the components shown in FIG. 2. For example system 200 described herein may be, or may include components of portable device 100. For example, by executing software or executable code 125 stored in memory 120, controller 105 may be configured to carry out a method of predicting a healthcare event as described herein. For example, controller 105 may be configured to receive classifying personal information (e.g., one or more personal parameters) for a plurality of persons (Such personal parameters may include, for example, age, height, weight, gender, ethnic association, fitness level, medical condition, and/or any other information that may be used in order to classify or associate a person to a physiological cluster.).

As used herein a cluster may include for example a group of people having one or more similar personal parameters and/or personal parameters in the same set of ranges. The personal parameters may include general parameters such as, age range, gender, ethnic association, etc. and/or physiological parameters, such as height range, weight range, BMI range, fitness level, medical condition and the like. Accordingly, a person may be associated with a specific cluster if one or more of his personal parameters is similar or within the range of parameters defined in the cluster. For example, a cluster may include females, aged 45-55 having BMI higher than 28 diagnosed with high blood pressure. A woman included in this cluster may be known from general medical knowledge or statistical knowledge to have a higher risk of being diagnosed with a heart disease than other women, in other clusters.

Controller 105 may further collect via one or more sensors 135, measurements or levels of health parameters indicators, such as heartbeat rate, blood pressure, oxygen saturation in a person's blood, $CO_2$ level in a person's blood, respiration rate and the like. Controller 105 may further create a personal physiological pattern profile for one or more persons, associate each person to a physiological cluster, create for each physiological cluster a health indicator deviation pattern for at least one healthcare event and use the collected data (e.g. classifying personal information, health indicators measurements etc.), the cluster information and the health indicator deviation pattern to predict the expected occurrence of a healthcare event as described herein.

Operating system 115 may be or may include any code segment (e.g., one similar to executable code 125 described herein) designed and/or configured to perform tasks involving coordination, scheduling, arbitration, supervising, controlling or otherwise managing operation of portable device 100, for example, scheduling execution of software programs or enabling software programs or other modules or units to communicate. Operating system 115 may be a commercial operating system.

Memory 120 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 120 may be or may include a plurality of possibly different memory units. Memory 120 may be a computer or processor non-transitory readable medium, or a computer non-transitory storage medium, e.g., a RAM.

Executable code 125 may be any executable code, e.g., an application, a program, a process, task or script. Executable code 125 may be executed by controller 105 possibly under control of operating system 115. For example, executable code 125 may be an application that performs methods as further described herein. Although, for the sake of clarity, a single item of executable code 125 is shown in FIG. 1, a system according to embodiments of the invention may include a plurality of executable code segments similar to executable code 125 that may be loaded into memory 120 and cause controller 105 to carry out methods described herein.

Storage 130 may be or may include, for example, a hard disk drive, a universal serial bus (USB) device or other suitable removable and/or fixed storage unit. In some embodiments, some of the components shown in FIG. 1 may be omitted. For example, memory 120 may be a non-volatile memory having the storage capacity of storage 130. Accordingly, although shown as a separate component, storage 130 may be embedded or included in memory 120.

Input/output devices 140 may be or may include input units such as: a mouse, a keyboard, a touch screen or pad, one or more sensors or any other or additional suitable input device. It will be recognized that any suitable number of input devices may be operatively connected to portable device 100 as shown by block 140. Input/output devices 140 may further include output means such as: one or more displays or monitors, speakers and/or any other suitable output devices.

Figure 2:
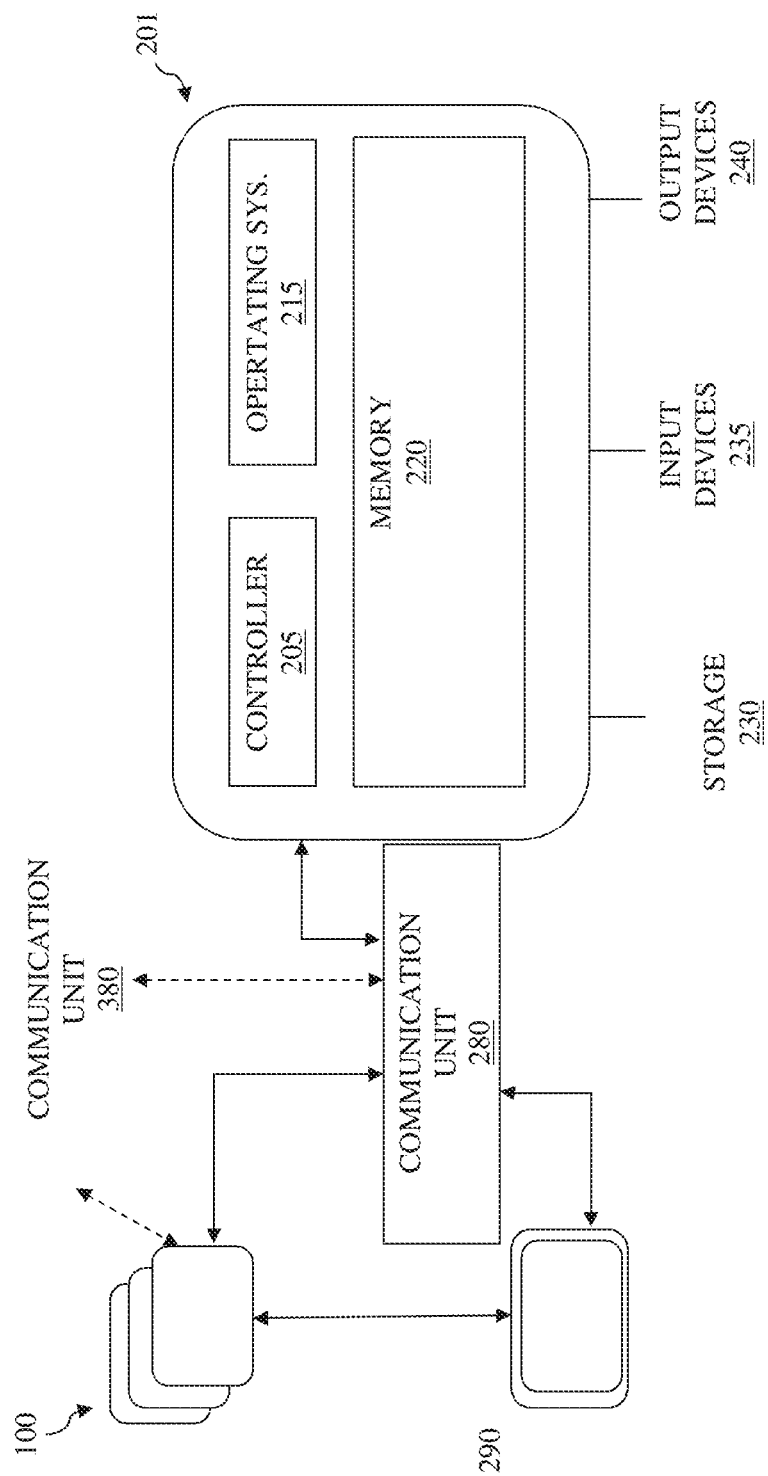
FIG. 2 shows high level block diagram of a system for predicting a healthcare event according to an embodiment of the present invention.

Reference is now made to FIG. 2 which is a high level block diagram of a system 200 for predicting a healthcare event according to embodiments of the present invention. System 200 may have a plurality of portable devices 100, and one or more server computers 201. Server computer 201 may include a main controller 205 that may be, for example, a central processing unit processor (CPU), a chip or any suitable computing or computational device, an operating system 215, a memory 220, an executable code 225, a storage 230, input devices 235 that may be, for example, a keyboard, a mouse, a keypad, or any other suitable input device. Main controller 205 may be similar to controller 105 of portable device 100 and may be configured to carry out methods described herein, and/or to execute or act as the various modules, units, etc. In some embodiments, system 200 may further include a communication unit 280 for communicating with portable devices 100 via a communication network, such as, for example, the Internet.

In some embodiments, communication unit 150 of portable device 100 may be configured to communicate with communication unit 280, via an intermediate communication unit 380. For example, intermediate communication unit 380 may be located in relative proximity to portable device 100, for example, in the same room as portable device 100. In some embodiments, intermediate communication unit 380 may use a first communication protocol to communicate with communication unit 150 (e.g., Bluetooth, Wi-Fi, or the like) and a second communication protocol to communicate with remote communication unit 280, for example, an internet protocol.

Executable code 225 may be any executable code, e.g., an application, a program, a process, task or script. Executable code 225 may be executed by main controller 205 possibly under control of operating system 215. For example, executable code 225 may be a program that performs methods as further described herein. A system according to embodiments of the invention may include a plurality of executable code segments similar to executable code 125 and 225 that may be loaded into memory 120 and 220 and cause controller 105 and/or main controller 205 to carry out methods described herein.

Storage 230 may be or may include, for example, a hard disk drive, a universal serial bus (USB) device or other suitable removable and/or fixed storage unit. In some embodiments, some of the components of server computer 201 shown in FIG. 2 may be omitted. For example, memory 220 may be a non-volatile memory having the storage capacity of storage 230. Accordingly, although shown as a separate component, storage 230 may be embedded or included in memory 220.

Memories 120 and 220 and storage devices such as 130 and 230 may store data such as profiles, personal classifying information, physiological clusters, measurements of one or more health indicators.

According to some embodiments, one or more server computers 201 may be in active communication with one or more portable or mobile devices 100 via a communication unit 280 that may include a communication network, such as the Internet. According to some embodiments, one or more personal computing devices 290, such as a desktop computer, a laptop computer, a tablet or the like, may be also in active communication with one or more devices 100 and/or server computer 201. It should be appreciated that such personal computing devices 290 may serve as an input device for devices 100 and/or server computer 201.

Figure 3A:
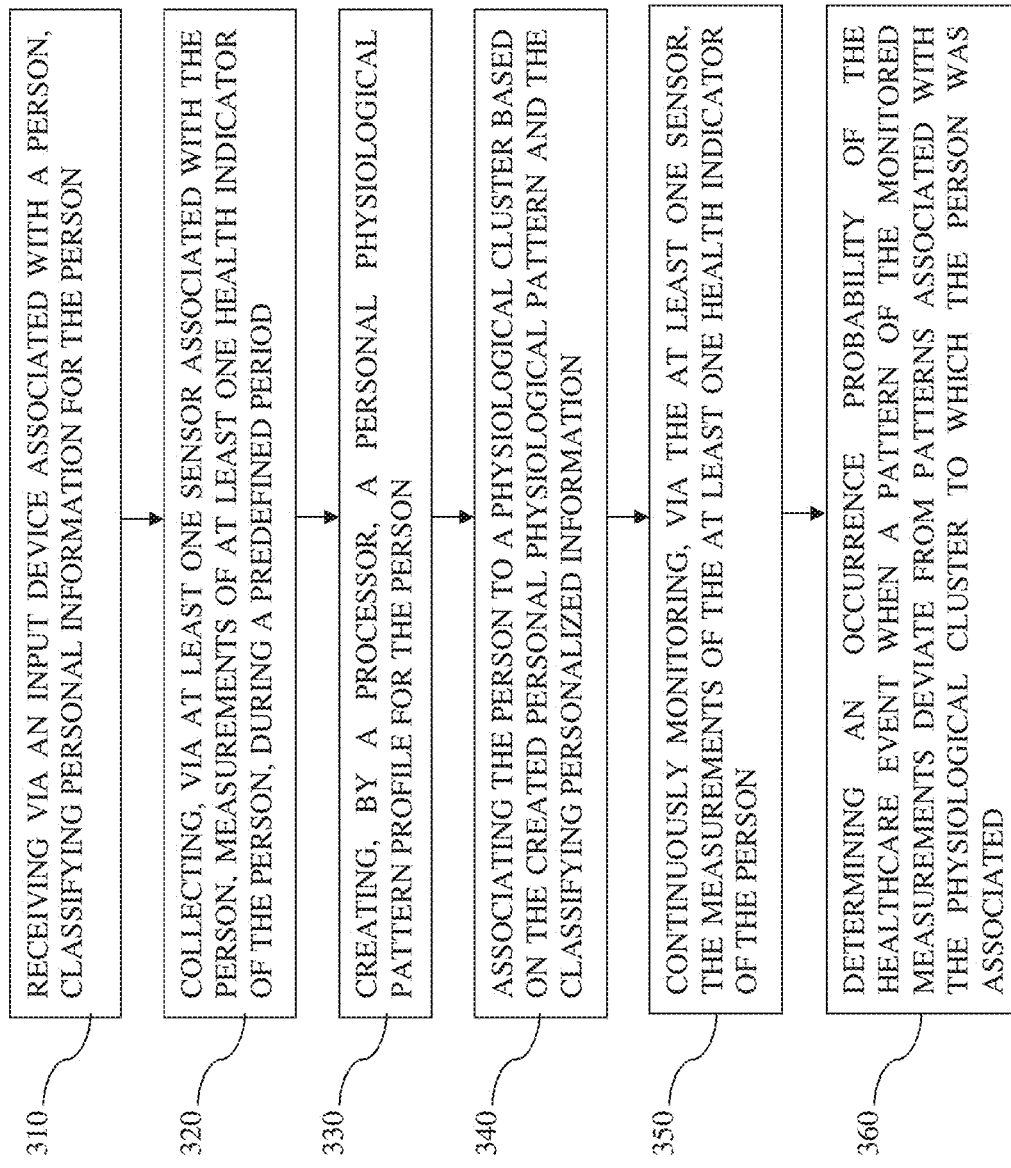
FIG. 3A is a flowchart of a method of predicting a healthcare event according to one embodiment of the present invention.

FIG. 3A is a flowchart of a method of predicting a healthcare event according to embodiments of the present invention. The embodiments of FIG. 3A may be performed by main controller 205, controller 105 or by any other suitable controller. In operation 310, classifying personal information for a person may be received via an input device associated with the person. Input devices according to some embodiments may include a keypad, a keyboard, a touchscreen, a microphone or any other input device suitable for providing classifying personal information about one or more persons. Classifying personal information may be or may include any information regarding one or more persons that may be used in order to classify or sort such person or persons into physiological clusters. Such classifying personal information may include, for example, age, weight, height, BMI, gender, nationality, ethnic association, fitness level, health condition, geographical location etc.

For example, a male, age 38, living in Bolivia, and indicated as suffering from being overweight (e.g. having a Body Mass Index (BMI) of 27) would, most probably have different health indicator values than an 18 years old Chinese female gymnast, and a different probability for a healthcare event. More so, changes in the measured values of some health indicators (such as, heartbeat rate, respiration rate, blood pressure, skin temperature etc.) may have a different normal range (that is, a range of values that is considered normal). Accordingly, a physiological cluster is a cluster or group of persons having similar expected physiological behavior in similar conditions. For example, people in the age range of 30-34 years with BMI in the range of 26-29, with low fitness level, and no known medical conditions, leaving in similar climatic conditions (similar altitude, similar humidity and temperature averages etc.) and working in similar conditions (e.g. office work, physical work etc.), may be associated or clustered to the same physiological cluster or group, as it may be expected that such people may have similar physiological behavior in similar conditions. That is, that their health indicators would have normal values within similar ranges in similar conditions.

It should be appreciated that the classifying personal information may be received via an input device of a portable or mobile device 100 (e.g. a wearable computing device such as a bracelet-like computing device, a smart watch, a smartphone and the like) and/or via a personal computer (device 290 in FIG. 2) or any other computing device that may be associated with the portable or mobile device 100 and/or with the server computer, via a website, an application or in any other way known in the art, and having known input devices, such as a keyboard, a touchscreen, a mouse or any other input device suitable for providing classifying personal information to the portable or mobile device and/or to the server computer.

In operation 320, measurements of at least one health indicator of the person may be collected via at least one sensor (e.g., sensor 135) associated with the person. The measurements may be collected during a predefined learning period or time. It should be appreciated that the length or duration of the learning period may change according to the health indicator and the physiological cluster to which the person is associated. For example, the learning period may vary from 0 (i.e. no learning time is required) to a few hours, a few days, a month or even a few months, depending on the type of health indicator, the cluster to which the person is associated, the activity profile of the person and the like. For example, blood pressure measurements may be collected from 24 hours up to 7 days for relatively healthy 75-85 years old males, however, collecting acceleration measurements from fall events may take more than 6 month for the same age group.

During the learning period continuous or repeated measurements of one or more health indicators may be collected and recorded in a storage or memory of a portable device (e.g., storage 130 and/or memory 120) and/or a remote server computer (e.g., e.g., storage 230 and/or memory 220) and the person's normal range of health indicator or indicators values may be calculated by a processor or controller of either portable device 100 or the remote server computer (e.g., system 200) with which the portable device is in active communication. The normal range may be defined as the average value calculated during the learning period and a predefined standard deviation around the average value. In some cases the normal range may be defined by healthcare organizations. For example, normal body temperature is defined as a body temperature in the range of 36.5-37.2 degrees Celsius. Normal pulse or heartbeat rate for healthy adults may range from 60 to 100 beats per minute. Females ages 12 and older, in general, tend to have faster heart rates than do males of the same age. Athletes, such as runners, who do a lot of cardiovascular conditioning, may have heart rates near 40 beats per minute. Thus, the normal heartbeat rate range of a person may be determined based on the association of the person to a specific cluster or group, such as adult male or female athlete.

In operation 330, embodiments may include creating (e.g., by controller 105 or controller 205) a personal physiological pattern profile for at least one person, based on the collected data received from the one or more sensors (e.g., sensor 135) and the received classifying personal information stored in a memory or storage of the portable device (e.g., device 100) or the server computer (e.g., server computer 201). Pattern profiles may be generated via a combination of, for example, averaged heart rate (HR)/HR variability/weekly activity/galvanic skin response (GSR), and the like. An example profile is illustrated in table 1 below:

TABLE 1 example profile

Profile ID: 123456

| Gender: Male | Weight: 70-75 Kg<br>Min. value | Height: 170-175 cm<br>Max. value |
|---|---|---|
| HR at rest (beat per min.) | 50 | 60 |
| HR active (beat per min.) | 100 | 120 |
| HRV at rest (ms) | 50 | 60 |
| HRV active (ms) | 50 | 60 |
| Body temperature (° C.) | 36.0 | 36.5 |

The profiles may include for example a gender, age group, weight range, height range and the minimum and maximum values of one or more health indicators, for example, the health indicators listed in table 1.

In operation 340, the person may be associated (or assigned) with or to a physiological cluster based on the created personal physiological pattern and the classifying personalized information.

According to some embodiments a method may further include creating, for each physiological cluster, a health indicator deviation pattern for one or more healthcare events, based on values of the at least one health indicators measured during a predefined time period prior to the occurrence of healthcare events for which the health indicator deviation pattern is created, of persons associated with the cluster. As used herein, a deviation pattern may include a detected change (or changes) in health indicators of one or more persons associated with a cluster following/during the same healthcare event. In some embodiments, such detected changes may using similar changes detected in health indicators in other members of the cluster in order to determine that the other members had the same healthcare event. For example, information collected regarding changes in health indicators' values of persons associated to a mutual cluster, that suffered a specific healthcare event (e.g. a cardiac arrest event) during a predefined time period prior to the occurrence of the event, may serve to create a deviation pattern of each health indicator, for the specific mutual cluster.

In operation 350, the measurements of the at least one health indicator of the person may be monitored (e.g., continuously, or repeatedly (e.g., regularly)), via the at least one sensor.

In operation 360, an occurrence probability of the healthcare event may be determined when a pattern of the monitored measurements deviate from patterns associated with the physiological cluster to which the person was associated, received from a database. Patterns of the one or more health indicators of one or more persons may be compared to patterns associated with the physiological cluster to which the person was associated. For example, if a person's heartbeat rate exceeds by, for example 20%, the person's maximum normal heartbeat rate (e.g. the person's pulse reaches 120 beats per minute) the person's body temperature indicates that the person has fever (e.g. has a body temperature of above 37.2 degrees Celsius) and the person is not physically active (e.g. at rest), and the aforementioned deviation from the normal range is similar to the deviation pattern known to indicate a viral influenza event in members of the same cluster or group to which the person is associated, then a prediction of the probability of a viral influenza event may be calculated.

Figure 3B:
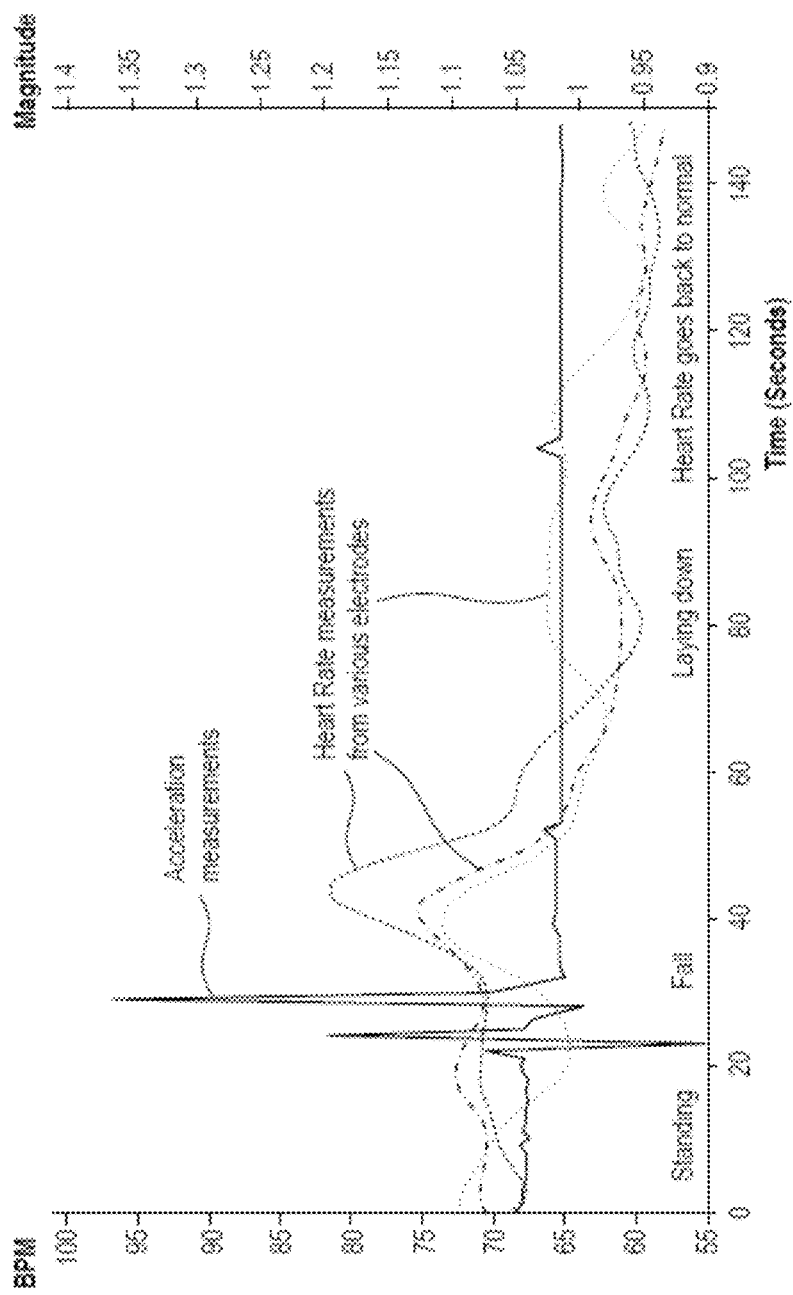
FIG. 3B is a graph showing acceleration and heart rate measurements of a person during a fall event according to some embodiments of the invention.

In another example, some measured health indicators may lead to the calculation of a high probability for the occurrence of a fall event (where the person has fallen). When an accelerometer worn by the person (e.g., an accelerometer included in portable device 100) measures a sharp deviation from "normal activities" such as sitting, standing or walking, followed by a physiology signals' transition phase and then an indicator that the person is laying down, a potential "fall event" trigger may be initiated. Graphs illustrating the measured deviations in acceleration and heart rate are given in FIG. 3B. As can be seen, there is a sharp increase in the measured acclamation during a fall followed by a "laying down" period of almost no acceleration. Controller 205 (or controller 105) may calculate the probability of the fall event based on measured indicators. Additional indicators, such as, heart rate and blood pressure may also be included in the calculation. For example, the heart rate may increase by more than 50% during the fall event transition, as can be seen in FIG. 3B.

According to some embodiments a method may include receiving additional data related to the person and adjusting the determined occurrence probability of the healthcare event base on the additional data. In some embodiments, the additional data may include at least one of: date, time, location, ambient temperature and ambient humidity. These parameters may be received from elements (e.g., controller 105) and/or sensor or sensors included in mobile device 100 (e.g., sensor 135). Additionally, or alternatively, the parameters may be received from additional devices, for example, a mobile phone associated with portable device 100 or communication unit 380. One or more sensors may be included in the mobile device or connected to communication unit 380. In some embodiments, at least some of the parameters may be received from a remote database.

In some embodiments, the received additional data may be related to the general wellbeing of the person. A data related to the general wellbeing of the person may include, the medications taken by the person, if he/she is living with a partner (e.g., a spouse or a caregiver), whether the person is using a walking stick or a walker, how many time in the past (e.g., the past 3/6 months) the person suffered from the healthcare event (e.g., fall) or the like. In some embodiments, each of the parameters related to the general wellbeing of the person may be assigned with an initial score (e.g., for example by the professional, or using a known data stored in lookup tables) and an embodiment may include ongoing process of updating the scores, when one of the parameters changes. For example, the system may automatically update the score of the numbers of past fall events after another fall event was detected by the system. In yet another example, the system may receive from the person's caregiver a list of updated medications every time the doctor changes at least one medication.

According to some embodiments a method calculating the occurrence probability based on the scores assign for each parameter and updating the occurrence probability of the healthcare event when the score of at least one parameter was updated. For example, the occurrence probability of a fall event may increase when the person was given sleeping pills for treating a sleeping disorder. In yet another example, the occurrence probability of a fall event may increase when the person becomes a widow and starts living by herself.

In some embodiments the fall event detection threshold may be automatically adjusted according to the dynamic risk scoring mentioned above.

An example of the used of the additional data in adjusting the determined occurrence probability of the healthcare event may be given with respect to detection of early stages of dehydration. If the received additional data may indicate that unusually hot and dry conditions are accepted or currently measured in the vicinity of the person, controller 205 (or 105) may be configured to closely monitor health indicators, such as, body temperature, heart rate and mobility and compare them with patterns of the health indicators collected from the same classified group of persons during normal condition. In some embodiments, is the person was classified into a cluster of persons suffering from renal problems, an alert may be given to the person or a caregiver to perform a urine test in addition to the monitored health indicators in order to determine if the person suffers from dehydration.

According to some embodiments a method may further include general detection of abnormal activity, for example, in elderly people. In such a case the measured health indicators (e.g., a pattern of the measured indicators) may be compared with stored patterns of health indicators gathered from persons classified to the same group under normal conditions (e.g., in good health). In some embodiments, additional factor such as the time in the day and the day (e.g., season) in the year, the ambient temperature and humidity, when the measurements were taken may further be considered when selecting to which stored pattern the measured pattern may be compared. For example, measurements taken from 80 years old lady during mid-summer at 11:00 in the morning may be compared with stored patterns for ladies age 75-85 taken in the summertime between 09:00-12:00. In some embodiments, simultaneous changes in more than two standard deviation of of the det detected health indicators (e.g., HRV, HR, GSR, Skin temperature and the like) may be mathematically combine with additional parameters, such as, the user activity intensity, sleeping hours and local weather (like extreme summer or winter time) in order to calculate the probability.

An occurrence probability of a healthcare event may be calculated as weighted average of monitored indicators values or patterns. For example, a flu occurrence probability may be calculated as a weighted average of skin temperature gradient, Heart Rate Variability (HRV) and sleep hours variability. A healthcare event may be, according to some embodiments, a cardiac arrest event, a stroke event, a viral influenza event, a pre-eclampsia event, an oxygen drop event, high body temperature event (also referred to as overheating event), dangerous activity level event (e.g. too long activity, too intense activity etc. also referred to as over active event), fall event, pre-dehydration event, abnormal physiologic deviation event, and anxiety event.

As used herein a health indicator may be any detectable physiological parameter that can be either measured using a sensor such as sensor 135 and/or indicated by the person (e.g., I have a headache) or by another person (e.g., a caregiver indicating that the person is pale). Health indicators according to some embodiments, may include for example heartbeat rate, heart rate variability, respiration rate, acceleration, location, movement, galvanic skin response (GSR), oxygen saturation, $CO_2$ blood level, skin temperature, sleeping hours, blood pressure, and physiological state. According to some embodiments, the physiological state may be received from the at least one person via the input device of the portable/mobile device, or from any device associated therewith. The physiological state may include of one or more of: rest, moderate activity, intense activity such as, participation in a sport competition, and the like.

Figure 3C:
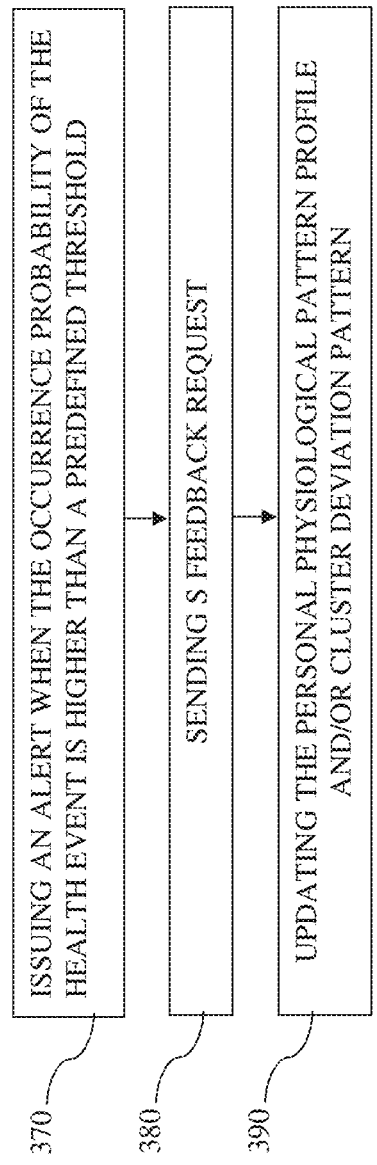
FIG. 3C is flowchart of a method of utilizing the predicted healthcare event according to one embodiment of the present invention.

FIG. 3C is a flowchart of a method of utilizing the predicted healthcare event according to one embodiment of the present invention. The embodiments of FIG. 3C may be performed by controller 205 of system 200 or by any other suitable controller. In operation 370, an alert may be issued when the occurrence probability of one or more health events is higher than a predefined threshold. For example, if the calculated probability to the occurrence of a health event is higher than 50%, an alert may be issued to at least one of: a caregiver, a family member of the person and the person. The alert may be a vocal alert, a text alert a visual alert or any other type of alert suitable for informing the person that he or she are at risk. In some embodiments, when occurrence probability of one or more health events is higher than a predefined threshold the controller may operate a microphone that may allow the controller to further record sounds made by the person (e.g., aching sounds, no sounds, crying etc.). The microphone if associated with an audio device may allow to further communicate with the person, for verbally assessing the persons condition. According to some embodiments, a higher threshold may be set, such as for example, a probability of 70%, 85% (or even higher) to suffer a healthcare event to avoid non-serviceable false alerts rate. The alert may include recommendations to the person, the caregiver and/or the family member as to how to avoid the healthcare event, such as, for example "approach the family doctor for anti-viral prescription" during early detection of Influenza, or increase water consumption in case of early detection of dehydration.

According to some embodiments, an alert may be sent to a healthcare provider such as a medical insurance agency, a medical facility, a hospital, a first aid organization and the like, as well as to family members, caregivers and the like. It should be appreciated by those skilled in the art that if a healthcare event occurs, an alert may also be sent to one or more of the above healthcare providers as well as to emergency agencies. According to some embodiments, the event alert may include information regarding the type of the event, the health indicators measured before, during and/or after an event and the location of the person having the healthcare event. It should be appreciated that other or additional information may be sent together with the event alert as may be preset or as may be required according to the type of the event, the severity of the event and other parameters, such as, for example, location of the person, medical history of the person and the like.

In operation 380, a feedback request may be sent when a deviation from the at least one person's personal physiological pattern profile is identified. Such feedback request may include requesting the person to provide additional information regarding his or her condition or how they are feeling, requesting additional health indicators measurements, test results and the like. An embodiment may further include, according to some embodiments, measuring additional health indicators based on measured health indicators and the feedback received from the at least one person. For example, when the calculated probability of suffering an arrhythmias event is higher than a predefined threshold, recommend the user to go through an electrocardiogram (ECG) measurement and be seen by a cardiologist.

In operation 390, the personal physiological pattern profile of the at least one person may be updated based on monitored health indicators and healthcare events history.

According to some embodiments, a method may further include updating the physiological cluster's deviation pattern of the healthcare event based on the at least one health indicator's values measured during a predefined time period prior to the occurrence of each healthcare event. It should be appreciated that an indication that the healthcare event has occurred may be received from a health maintenance or insurance provider, doctor, from at least one person (e.g. the person having the healthcare event, a caregiver, a passerby, a medical provider team member or the like) and/or from any other healthcare organization or institute.

Figure 4A:
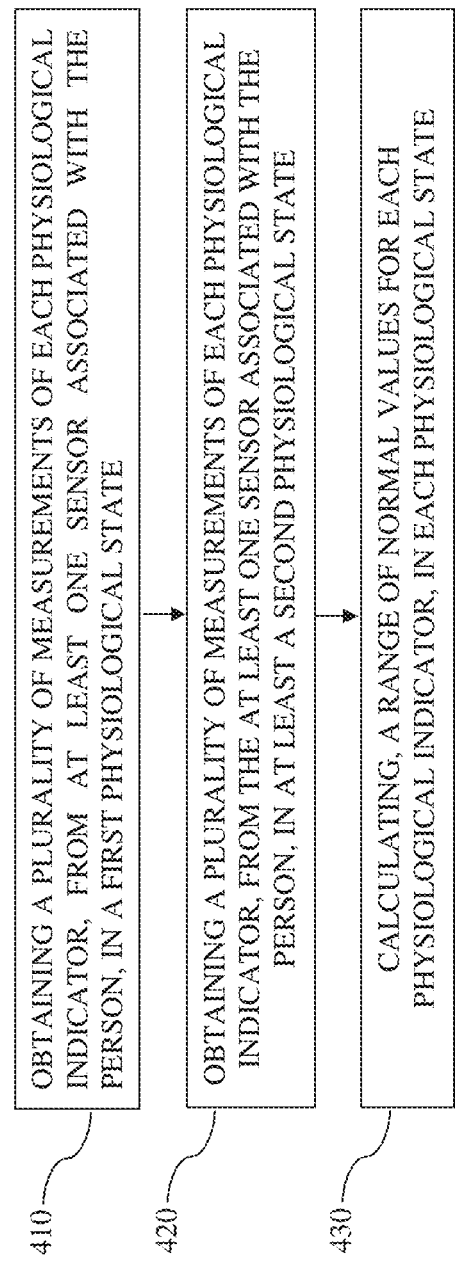
FIG. 4A is a flowchart of a method of creating a personal physiological pattern profile according to some embodiments of the present invention.

FIG. 4A, is a flowchart of a method of creating a personal physiological indicators profile according to some embodiments of the invention. The embodiments of FIG. 4A may be performed by controller 205 of system 200, controller 105 of portable device 100 or by any other suitable controller. In operation 410, a plurality of measurements of each physiological indicator may be obtained, from a portable device (e.g., device 100), in a first physiological state. For example, controller 205 may receive from portable device 100, a first set of healthcare indicators, within 15 minutes from the person's awakening when the person is considered to be in a normal health condition. In operation 420, embodiments may include obtaining a plurality of measurements of each physiological indicator, from the portable device, in at least a second physiological state. For example, controller 205 may receive from portable device 100 a second set of healthcare indicators, within 15 minutes after the person's finished his/her lunch, when the person is considered to be in a normal health condition.

In operation 430, calculating a range of normal values (or normal patterns) for each physiological indicator may be preformed, in each physiological state, based on the obtained measurements received, for example from by the wearable accelerometers' readings and the mobile handsets' accelerometers' readings (e.g. as a weighted average of the readings) and based on the one or more clusters to which the at least one person is associated. As used herein, the range of normal values may include measurements or data extracted from the measurements (e.g., minimum, maximum, average, standard deviation (STDV), etc.) obtained when the person was relatively healthy (e.g., was not diagnosed with new illnesses or healthcare events), as indicated for example, by his/her personal physician. For example, blood pressure or heart rate measurements that where taken from a person diagnosed with diabetes and chronic high blood pressure during a period of time when the person was not diagnosed with new healthcare events (e.g., a flu or a fall event) may be considered as "normal values" for that person.

Figure 4B:
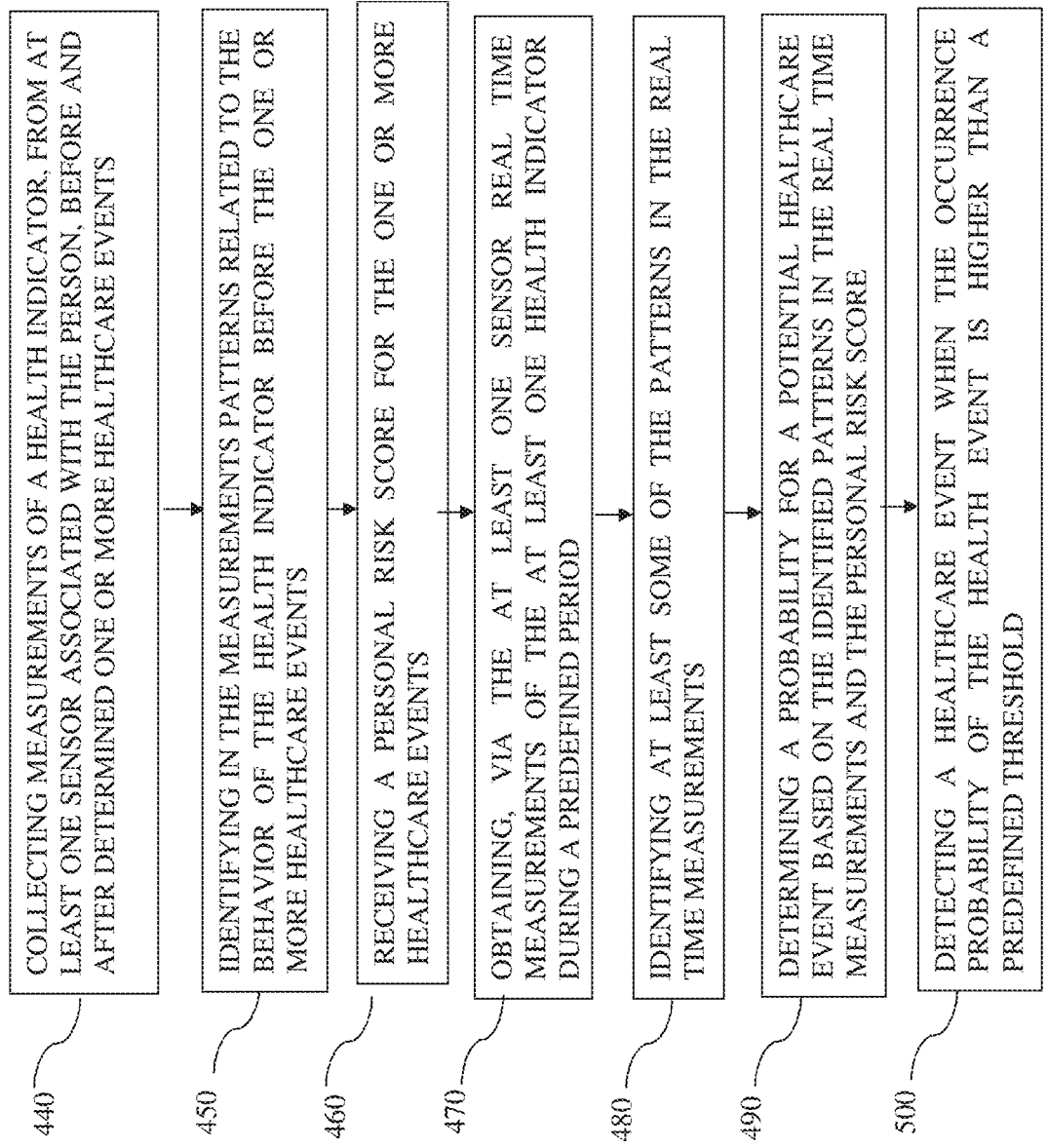
FIG. 4B is a flowchart of a method of determining a probability for a potential healthcare according to some embodiments of the invention.

The assignment or association of a person to a cluster may be based, according to some embodiments of the present invention, on combination of personal chronic diseases backgrounds and at least one of: gender, weight, height, age, ethnic association, fitness level, rest/activity vital signs ranges, daily and weekly activity levels, BMI and the collected values of said one or more health indicators. For example, FIG. 4B is a flowchart of a method of determining a probability for a potential healthcare according to some embodiments of the invention. The embodiment of FIG. 4B may be performed by controller 205 of system 200, controller 105 of portable device 100 or by any other suitable controller. In operation 440, measurements may be collected of a health indicator, from at least one sensor associated with the person, before and after determined one or more healthcare events. The measurements may be collected according to any one of the embodiments disclosed herein, for example, as discussed in operation 320 of the embodiments of FIG. 3A. In some embodiments, a health care event may be determined using at least some of operations 310-130 of the embodiments of FIG. 3A. For example, a healthcare event may be determined to exist or have occurred when the occurrence probability of one or more health events is be higher than a predefined threshold, as explained and discussed with respect to operation 370 of the embodiments of FIG. 3C.

An example of collected measurements of health indicators before and after a fall event according to some embodiments of the invention is given in FIGS. 5A-5E. FIG. 5A is a graph presenting the acceleration of device 100 or sensor 135 as a function of time. FIG. 5B is a graph presenting the galvanic skin response (GSR) as a function of time. FIG. 5C is a graph presenting the heartrate as a function of time. FIG. 5D is a graph presenting the heart rate variability (HRV) as a function of time and FIG. 5E is a graph presenting steps walked by the person. The fall event in each graph is indicated by the dashed line. The fall event was identified according to some embodiments of the invention, for example, when a sharp deviation from "normal measurements" may be detected and the occurrence probability of one or more health events is higher than a predefined threshold. As shown in the graph of FIG. 5A after the fall event, a sharp rise in the acceleration followed by a complete lack of motion may be detected. Furthermore, a sharp rise in the galvanic skin response was detected, in the graph of FIG. 5B, as well as a sharp incline followed by a sharp decline of the heartrate and a sharp decline of the heartrate variability following the fall event in the graphs of FIGS. 5C and 5D respectively.

Accordingly, all the measurements of the health indicators (e.g., acceleration, GSR, heartrate, heartrate variability, etc.) prior to the fall event may be recorded.

In operation 450, patterns related to the behavior of the health indicator before the one or more healthcare events may be identified in the measurements. For example, the patterns in the graphs of FIGS. 5A-5E before the fall event may be identified. As used herein, identifying a pattern may include identifying one or more typical parameters of the measurements, for example, the average, the standard deviation, the maximum and/or minimum of each graph, the general behavior (e.g., inclining/declining) and the like.

In operation 460, a personal risk score for the one or more healthcare events may be received, for example, from storage 130 or 230. In some embodiments, the personal risk score may be calculated according to established geriatric or chronic diseases medical evaluation scores, which may be dynamically updated by controller 205 or 105 and stored in storage 230 or 130. In some embodiments, the personal risk score may be calculated by giving different scores to two or more parameters associated with the person and conducting any mathematical manipulation (e.g., summing, multiplying, etc.) to the these parameters to calculate the risk score. For example, suffering from a chronic disease may be assigned with an x score, being over 85 years old a y score, using walking aids z score and living alone a q score. Accordingly, a 85 years old man, using a walking stick, living alone and having high blood pressure may have a q+x+y+z=risk score. In some embodiments, the personal risk score may include at least some of the parameters included in the personal physiological pattern profile disclosed herein. In some embodiments, the parameters for calculating the personal risk score may further include fall events' history, chronic diseases, medication usage and more. In some embodiments, the personal risk score may be dynamically updated, for example, based on data received from the system data base updates, such as personal auto-detected falls, new chronic diseases and medication change, updated into the user profile by the caregiver. In some embodiments, the personal risk score may further include hours in the day at which a particular person had healthcare events, based for example, on previous recordings of healthcare events. In some embodiments, the parameters for calculating the personal risk score may further include months at which the particular person had healthcare events, based for example, on previous recordings of healthcare events.

In operation 470, real time measurements may be obtained via the at least one sensor of the at least one health indicator during a predefined period. The measurements may be obtained from one or more sensors 135 according to any one of the embodiments disclosed herein, for example, as disclosed in operation 320 of the embodiments of FIG. 3A. Examples of such obtained measurements are given in the graphs of FIGS. 6A-6E which were measured during the sleeping hours (e.g., between 00:46 until 04:06). The real time measurements are represented by the grey circles. FIG. 6A is a graph presenting the GSR. FIG. 6B is a graph presenting the heart rate. FIGS. 6C and 6D are graphs presenting the standard deviation of the heart rate variability (HRVSDNN) and the root mean square of successive differences of the heart rate variability (HRVRMSSD) respectively. FIG. 6E is a graph presenting the skin temperature.

In operation 480, at least some of the patterns may be identified in the real time measurements. For example, patterns such as the average over a predefined time period (e.g., 15 minutes) may be dynamically calculated and compared to the data or patterns for identified patterns obtained before the occurrence of a healthcare event, for example, the patterns disclosed in FIGS. 5A-5D before the fall event. Accordingly, patterns of the GSR measurements of FIG. 6A may be compared to GSR patterns identified before the fall event FIG. 5B Similarly, the patterns in the heartrate measurements of FIG. 6B may be compared to the patterns identified in FIG. 5C. The comparison may include, comparing for example, the average of each pattern, the STDV, a first time derivative and the like.

In operation 490, embodiments may include determining a probability for a potential healthcare event based on the identified patterns in the real time measurements and the personal risk score. In some embodiments, determining the probability may include setting at least two threshold values, one for the risk score and one for at least one comparison between identified patterns. Accordingly, if both the calculated risk score and the difference between the identified patterns are above the set threshold values, controller 205 or 105 may determine a high probability for the occurrence of the potential healthcare event. Additionally or alternatively, the probability may calculated also based on a data regarding previous healthcare events of the person. For example, if only one of the calculated risk score or the difference between the identified patterns may be above the corresponding threshold value, but the person has a history of having such a healthcare event, controller 205 or 105 may determine a high probability for the occurrence of the potential healthcare event.

Furthermore, if the probability that a potential healthcare event is likely to occur, the controller may further look at the personal risk score to see if other parameters, such as the time in the day and the persons' skin temperature (FIG. 6E) may increase the probability for a potential healthcare event.

In operation 500, if the determined probability is above a predetermined threshold value (e.g., at least one of the calculated risk score or the difference between the identified patterns is above the corresponding threshold value and/or the person has a history of the specific healthcare event), the controller may detect or determine the occurrence of the healthcare event and conduct one or more of several operations. For example, the controller may alert a caregiver, alert a medical professional, call an ambulance, contact the person (e.g., via a microphone included in device 100), call a family member and the like. If the determined probability is below the predetermined threshold value, controller 205 or 105 may continue monitoring the health indicators to detect any abnormality.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of determining an occurrence probability of a healthcare event comprising:
    receiving via an input device associated with a person, predefined classifying personal information for the person;
    collecting, via two or more sensors associated with in contact with the person, real time measurements of two or more health indicators of the person during a predefined period;
    dynamically identifying, by a controller in communication with the input device and the two or more sensors, patterns in the real time measurements;
    creating, by the controller, a personal physiological pattern profile for the person based on the identified patterns and the classifying personal information;
    associating the person with a predefined physiological cluster based on the created personal physiological pattern profile and the classifying personalized information, wherein the predefined physiological cluster comprises a group of persons having similar expected physiological behavior in similar conditions;
    continuously monitoring, via the two or more sensors, the measurements of the two or more health indicators of the person;
    comparing, by the controller, the identified patterns in the real time measurements with patterns obtained before the occurrence of a healthcare event;
    determining, by the controller, an occurrence probability of the healthcare event when the identified patterns deviate from physiological patterns associated with the predefined physiological cluster the person is associated with;
    sending a feedback request when a deviation from the created personal physiological pattern profile is identified;
    updating the created personal physiological pattern profile of the person based on monitored health indicators and healthcare events history, and based on the received feedback;

when the healthcare event occurs, updating the predefined physiological cluster's deviation pattern of the healthcare event based on the two or more health indicator's values measured during a predefined time period prior to the occurrence of the healthcare event; and for an occurrence probability that is higher than a predefined threshold, transmitting a signal indicative that the healthcare event has occurred via, the controller, to a computing device.

2. The method of claim 1, wherein determining an occurrence probability of the healthcare event is based on a deviation pattern of monitored measurements of the two or more health indicators typical of the healthcare event.

3. The method according to claim 1, wherein the database includes health indicators of a plurality of persons each associated with a physiological cluster based on each person's personal physiological pattern profile and the classifying personal information of each of the plurality of persons.

4. The method of claim 3, wherein the database further includes a lookup table associating physiological clusters with health indicator deviation patterns expected at each healthcare event,
wherein each healthcare event was created based on values of two or more health indicators measured during a predefined time period prior to the occurrence of healthcare events of persons associated with the cluster.

5. The method according to claim 1, wherein said healthcare event is at least one of: cardiac arrest, stroke, viral influenza, pre-eclampsia, oxygen drop, overheating, over active, fall, dehydration, abnormal physiologic deviation and anxiety.

6. The method according to claim 1, wherein said two or more health indicators consist of one or more of: heart rate, heart rate variability, respiration rate, acceleration, location, movement, Galvanic Skin Response (GSR), oxygen saturation, $CO_2$ blood level, skin temperature, sleeping hours, blood pressure, and physiological state.

7. The method of claim 6, wherein said physiological state is received from the at least one person via the input device.

8. The method of claim 7, wherein the physiological state consists of one or more of: rest, moderate activity and intense activity, sport competition.

9. The method according to claim 1, wherein creating the personal physiological pattern profile comprises:
obtaining a plurality of measurements of each physiological indicator, from two or more sensors associated with the person, in a first physiological state;
obtaining a plurality of measurements of each physiological indicator, from two or more sensors associated with the person, in at least a second physiological state; and
calculating, by a controller, a range of normal values for each physiological indicator, in each physiological state, based on the obtained measurements and based on the one or more clusters to which the person is associated.

10. The method according to claim 1, wherein determining an occurrence probability is further based on previously recorded health indicators associated with previous healthcare events.

11. The method according to claim 1, comprising issuing an alert when the occurrence probability of the health event is higher than the predefined threshold.

12. The method of claim 1, further comprising determining additional health indicators based on measured health indicators and the feedback received from the person.

13. A system for determining an occurrence probability of a healthcare event comprising:
a first communication unit configured to receive health indicator values from a portable user device;
a database configured to store two or more of: health indicator values; physiological cluster information; physiological patterns, healthcare events information; and personal information of a plurality of persons; and
a main controller,
wherein the portable computing device comprises:
a controller;
two or more sensors adapted to measure two or more different health indicator values; and
a second communication unit configured to communicate with the first communication unit and transmit measured health indicator values to the main controller,
and wherein the main controller is configured to:
receive via an input device associated with a person, predefined classifying personalized information for the person;
collect, from the two or more sensors, real time measurements of the two or more health indicators of the person, during a predefined period;
dynamically identify patterns in the real time measurements;
create, a personal physiological pattern profile for the person based on the identified patterns and the classifying personal information;
associate the person to a predefined physiological cluster based on the created personal physiological pattern profile, wherein the predefined physiological cluster comprises a group of persons having similar expected physiological behavior in similar conditions;
continuously monitor, via the two or more sensors, the measurements of the two or more health indicators of the person;
compare the identified patterns in the real time measurements with patterns obtained before the occurrence of a healthcare event;
determine an occurrence probability of the healthcare event when the identified patterns deviate from physiological patterns associated with the predefined physiological cluster the person is associated with;
send a feedback request when a deviation from the created personal physiological pattern profile is identified;
update the created personal physiological pattern profile of the person based on monitored health indicators and healthcare events history, and based on the received feedback;
when the healthcare event occurs, update the predefined physiological cluster's deviation pattern of the healthcare event based on the two or more health indicator's values measured during a predefined time period prior to the occurrence of the healthcare event; and
for an occurrence probability that is higher than a predefined threshold, generate and transmit a signal indicative that the healthcare event has occurred to a computing device.

14. The system according to claim 13, wherein the portable computing device is a wearable device.

15. The system according to claim 13, wherein the two or more sensors are selected from: heart rate sensor, respiration rate sensor, oxygen saturation sensor, CO2 blood level sensor, motion sensor, accelerometer, Galvanic Skin Response (GSR) sensor, thermometer, a microphone, and blood pressure sensor.

16. The system according to claim 13, wherein the main controller is further configured to:
   receive additional data related to the person; and
   adjust the determined occurrence probability of the healthcare event base on the additional data.

17. The system according to claim 16, wherein the additional data is received from a sensor that includes at least one of: a GPS, an ambient temperature sensor and an ambient humidity sensor.

18. The method of claim 1, wherein the c signal is transmitted to at least one of: a user computing device associated with a caregiver, a user computing device associated with a professional, a computing device associated with an emergency service and a user computing device associated with a family member.

19. The method of claim 1, wherein comparing, by the controller, the identified pattern is also with patterns obtained at least during and after the occurrence of a healthcare event.

20. A system for determining an occurrence probability of a fall event comprising:
   a first communication unit configured to receive fall indicator values from a portable user device;
   a database configured to store one or more of: fall indicator values; physiological cluster information; fall patterns, fall events information; and personal information of a plurality of persons; and
   a main controller,
   wherein the portable computing device comprises:
      a controller;
      at least one motion sensor;
      at least one heartrate sensor; and
      a second communication unit configured to communicate with the first communication unit and transmit measured motion and heartrate values to the main controller,
   and wherein the main controller is configured to:
      receive via an input device associated with a person, predefined classifying personalized information for the person;
      collect, from the motion sensor and the heartrate sensor, real time motion measurements and real time heartrate measurements, during a predefined period;
      dynamically identify fall patterns in the real time measurements;
      create a personal fall pattern profile for the person based on the identified patterns and the predefined classifying personal information;
      associate the person to a predefined physiological cluster based on the created personal physiological fall pattern, wherein the predefined physiological cluster comprises a group of persons having similar expected physiological behavior in similar conditions;
      continuously monitor the real time measurements;
      compare the identified fall patterns in the real time measurements with fall patterns
      obtained before the occurrence of the fall event;
      determine an occurrence probability of the fall event when the identified personal fall pattern deviate from patterns associated with the physiological cluster, the person is associated with;
      send a feedback request when a deviation from the created personal fall pattern profile is identified;
      update the created personal fall pattern profile of the person based on monitored health indicators and healthcare events history, and based on the received feedback;
      when the healthcare event occurs, update the predefined physiological cluster's fall pattern of the healthcare event based on the two or more health indicator's values measured during a predefined time period prior to the occurrence of the healthcare event; and
      for an occurrence probability that is higher than a predefined threshold, generate and transmit a signal indicative that the fall event has occurred to a computing device.

21. The system of claim 20, wherein creating the personal fall pattern profile is based on identified patterns in motion measurements and heartrate measurements taken prior to the fall event and wherein determining the occurrence probability of the fall event includes predicting a fall event.

22. The system of claim 20, wherein creating the personal fall pattern profile is based on identified patterns in motion measurements and heartrate measurements taken prior to the fall event and following the fall event and wherein determining the occurrence probability of the fall event includes identifying a fall event.

* * * * *